(12) United States Patent
Kim et al.

(10) Patent No.: US 8,963,044 B2
(45) Date of Patent: Feb. 24, 2015

(54) PLASMA JET ASSEMBLY AND PLASMA BRUSH INCLUDING THE SAME

(75) Inventors: Yark Yeon Kim, Daejeon (KR); Han Young Yu, Daejeon (KR); Yong Ju Yun, Daejeon (KR); Won Ick Jang, Daejeon (KR); Eun-ju Jeong, Daejeon (KR); Changho Han, Daegu (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 245 days.

(21) Appl. No.: 13/615,393

(22) Filed: Sep. 13, 2012

(65) Prior Publication Data

US 2013/0153545 A1    Jun. 20, 2013

(30) Foreign Application Priority Data

Dec. 16, 2011  (KR) .......................... 10-2011-0136630

(51) Int. Cl.
*B23K 10/00*  (2006.01)
*H05H 1/30*  (2006.01)
*H05H 1/36*  (2006.01)

(52) U.S. Cl.
CPC .. *H05H 1/30* (2013.01); *H05H 1/36* (2013.01)
USPC .............. 219/121.5; 219/121.55; 219/121.48; 219/121.51; 315/111.51

(58) Field of Classification Search
CPC .............. H01J 37/32045; H01J 37/321; H01J 37/32137; H01J 37/32174; H05H 1/30; H05H 1/36
USPC ......... 219/121.5, 121.48, 121.51, 121.55, 75, 219/121.59
See application file for complete search history.

(56) References Cited

U.S. PATENT DOCUMENTS

| | | | | |
|---|---|---|---|---|
| 4,929,811 A | * | 5/1990 | Blankenship | 219/121.54 |
| 5,760,363 A | * | 6/1998 | Hackett et al. | 219/121.44 |
| 5,831,237 A | * | 11/1998 | Daniel | 219/121.54 |
| 5,837,958 A | * | 11/1998 | Fornsel | 219/121.5 |
| 6,013,075 A | * | 1/2000 | Avramenko et al. | 606/40 |
| 6,525,481 B1 | * | 2/2003 | Klima et al. | 315/111.21 |
| 2009/0065485 A1 | * | 3/2009 | O'Neill et al. | 219/121.52 |
| 2010/0301021 A1 | * | 12/2010 | Bohori et al. | 219/121.48 |
| 2013/0134890 A1 | * | 5/2013 | Richter | 315/200 R |

FOREIGN PATENT DOCUMENTS

JP  2008-098128 A  4/2008
JP  2008-181694 A  8/2008

* cited by examiner

*Primary Examiner* — Mark Paschall (57) ABSTRACT

Plasma jet assemblies are provided. A plasma jet assembly may include: a tube through which a gas flows; a power source providing a high frequency power exciting the gas in plasma state; a power electrode applying the high frequency power to the gas; and a plasma control unit removing arc discharge of a plasma gas generated in the tube by the high frequency power applied to the power electrode.

20 Claims, 5 Drawing Sheets

PLASMA JET ASSEMBLY AND PLASMA BRUSH INCLUDING THE SAME

CROSS-REFERENCE TO RELATED APPLICATIONS

This U.S. non-provisional patent application claims priority under 35 U.S.C. §119 to Korean Patent Application No. 10-2011-0136630, filed on Dec. 16, 2011, the entirety of which is incorporated by reference herein.

BACKGROUND

The inventive concept relates to medical devices and, more particularly, to plasma jet assemblies of medical devices and plasma brush including the same.

Biological effectiveness of low temperature atmospheric pressure plasma announced in the beginning of the 2000s and has been highlighted. The biological effectiveness of low temperature atmospheric pressure plasma has been widely applied to various devices such as air cleaners using microorganism-sterilization and harmful gas filters. Recently, announced research results about interaction of plasma and biological cells may activate new medical industries.

Stability according to a temperature and various structures according to medical treatment regions may be demanded for applying the atmospheric pressure plasma system to medical devices. A plasma generator may be easily manufactured using a plasma jet. However, a structure of the plasma jet may not be suitable to medical treatment of a wide region of the human body. Thus, it is required to develop medical plasma jet assemblies having various sizes and various shapes applied to a wider region.

SUMMARY

Embodiments of the inventive concept may provide plasma jet assemblies capable of increasing or maximizing stability of a plasma gas and plasma brushes including the same.

Embodiments of the inventive concept may also provide plasma jet assemblies capable of increasing or maximizing uniformity of a plasma gas and plasma brushes including the same.

In one aspect, a plasma jet assembly may include: a tube through which a gas flows; a power source providing a high frequency power exciting the gas in plasma state; a power electrode applying the high frequency power to the gas; and a plasma control unit removing arc discharge of a plasma gas generated in the tube by the high frequency power applied to the power electrode.

In some embodiments, the plasma control unit may include a resistor connected between the power source and the power electrode.

In other embodiments, the plasma control unit may further include a gas control valve controlling a flow rate of the gas flowing in the tube.

In still other embodiments, the gas control valve may be disposed at a gas supplying line connected to the tube.

In yet other embodiments, the gas supplying line may include a gas line and a connector.

In yet still other embodiments, the connector may include a pipe having channel holes through which the gas flows.

In yet still other embodiments, the pipe may include an insulating stick, and the channel holes may be disposed around the insulating stick.

In yet still other embodiments, the power electrode may include a needle disposed in the tube.

In yet still other embodiments, the power electrode may further include a cladding layer protecting the needle from the plasma gas.

In yet still other embodiments, the power electrode may include a metal ring surrounding the tube.

In yet still other embodiments, the plasma jet assembly may further include: a ground electrode formed at another side of the tube opposite to the power electrode.

In yet still other embodiments, the ground electrode may include a metal ring formed an end of the tube.

In yet still other embodiments, the tube may include a dielectric material.

In yet still other embodiments, the dielectric material may include alumina or ceramic.

In another aspect, a plasma brush may include: a frame; a power source providing a high frequency power; and plasma jet assemblies fixed at the frame, each of the plasma jet assemblies including a tube through which a gas flows, a power electrode applying the high frequency power to the gas, and a plasma control unit removing arc discharge of a plasma gas generated in the tube by the high frequency power applied to the power electrode.

In some embodiments, the plasma brush may further include: a common ground bar disposed another sides of the tubes.

In other embodiments, the plasma brush may further include: a cladding layer protecting the common ground bar from the plasma gas.

In still other embodiments, the plasma control units may include resistors connected between the power source and the power electrodes.

In yet other embodiments, the plasma control units may further include gas control valves controlling flow rates of the gas flowing in the tubes.

In yet still other embodiments, the plasma brush may further include: a common power electrode connected between the power source and the resistors.

BRIEF DESCRIPTION OF THE DRAWINGS

The inventive concept will become more apparent in view of the attached drawings and accompanying detailed description.

DETAILED DESCRIPTION OF THE EMBODIMENTS

The inventive concept will now be described more fully hereinafter with reference to the accompanying drawings, in which exemplary embodiments of the inventive concept are shown. The advantages and features of the inventive concept and methods of achieving them will be apparent from the following exemplary embodiments that will be described in more detail with reference to the accompanying drawings. It should be noted, however, that the inventive concept is not limited to the following exemplary embodiments, and may be implemented in various forms. Accordingly, the exemplary embodiments are provided only to disclose the inventive concept and let those skilled in the art know the category of the inventive concept. In the drawings, embodiments of the inventive concept are not limited to the specific examples provided herein and are exaggerated for clarity.

The terminology used herein is for the purpose of describing particular embodiments only and is not intended to limit the invention. As used herein, the singular terms "a," "an" and "the" are intended to include the plural forms as well, unless the context clearly indicates otherwise. As used herein, the term "and/or" includes any and all combinations of one or more of the associated listed items. It will be understood that when an element is referred to as being "connected" or "coupled" to another element, it may be directly connected or coupled to the other element or intervening elements may be present.

Similarly, it will be understood that when an element such as a layer, region or substrate is referred to as being "on" another element, it can be directly on the other element or intervening elements may be present. In contrast, the term "directly" means that there are no intervening elements. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Additionally, the embodiment in the detailed description will be described with sectional views as ideal exemplary views of the inventive concept. Accordingly, shapes of the exemplary views may be modified according to manufacturing techniques and/or allowable errors. Therefore, the embodiments of the inventive concept are not limited to the specific shape illustrated in the exemplary views, but may include other shapes that may be created according to manufacturing processes. Areas exemplified in the drawings have general properties, and are used to illustrate specific shapes of elements. Thus, this should not be construed as limited to the scope of the inventive concept.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concept explained and illustrated herein include their complementary counterparts. The same reference numerals or the same reference designators denote the same elements throughout the specification.

Moreover, exemplary embodiments are described herein with reference to cross-sectional illustrations and/or plane illustrations that are idealized exemplary illustrations. Accordingly, variations from the shapes of the illustrations as a result, for example, of manufacturing techniques and/or tolerances, are to be expected. Thus, exemplary embodiments should not be construed as limited to the shapes of regions illustrated herein but are to include deviations in shapes that result, for example, from manufacturing. For example, an etching region illustrated as a rectangle will, typically, have rounded or curved features. Thus, the regions illustrated in the figures are schematic in nature and their shapes are not intended to illustrate the actual shape of a region of a device and are not intended to limit the scope of example embodiments.

Figure 1:
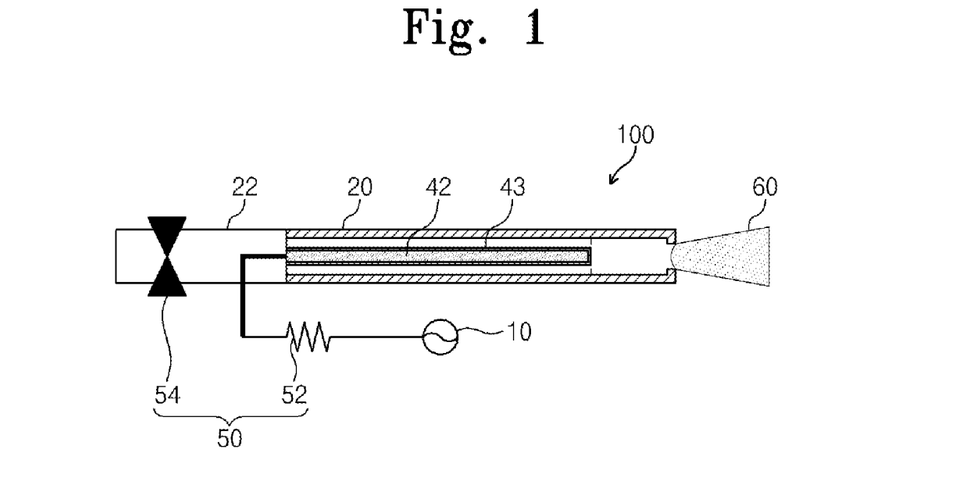
FIGS. 1 and 2 are cross-sectional views illustrating plasma jet assemblies according to some embodiments of the inventive concept.
Figure 2:
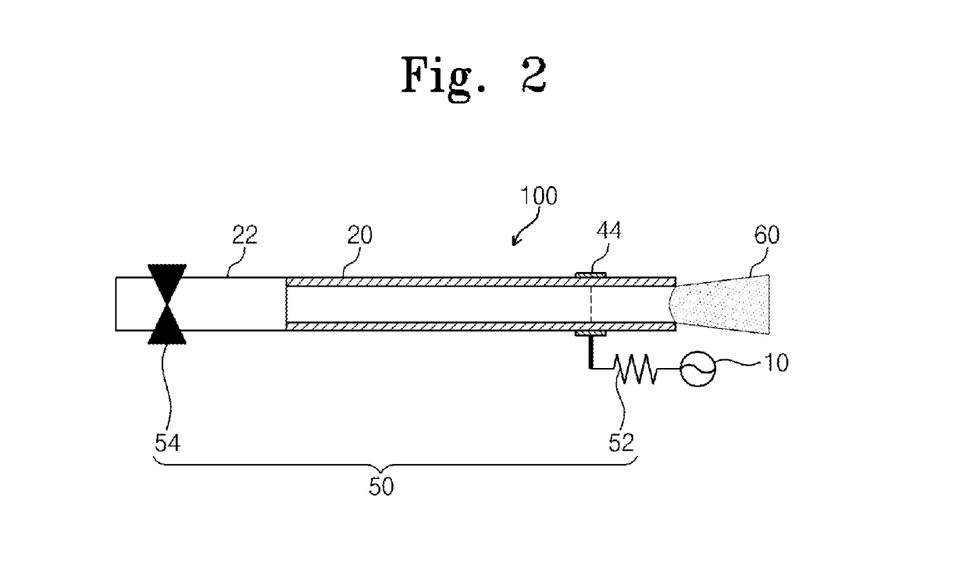

FIGS. 1 and 2 are cross-sectional views illustrating plasma jet assemblies according to some embodiments of the inventive concept.

Referring to FIGS. 1 and 2, a plasma jet assembly 100 according to some embodiments of the inventive concept may include a plasma control unit 50 removing arc discharge of a plasma gas 60 jetted from a tube 20. The plasma control unit 50 may include a resistor 52 controlling a high frequency power and a valve 54 controlling a flow rate of the plasma gas 60.

Thus, the plasma jet assembly 100 may increase or maximize stability of the plasma gas 60 by the removal of the arc discharge.

The tube 20 may flow a source gas and the plasma gas 60 supplied through a gas supplying line 22. The source gas may include a carrier gas and an activation gas. The carrier gas may include an inert gas such as a helium gas or an argon gas. The activation gas may include an oxygen gas or a nitrogen gas. The source gas may be excited in plasma state by a high frequency power applied from a power needle 42 of FIG. 1 or a power ring 44 of FIG. 2. Here, the source gas excited in the plasma state may be defined as a plasma plume or a plasma gas. Thus, the tube 20 may include a dielectric material (e.g., alumina or ceramic) having excellent corrosion resistance and/or excellent chemical resistance with respect to the plasma gas.

The tube 20 may include a nozzle which converts pressure-energy of the source gas supplied through the gas supplying line 22 into speed-energy to rapidly releasing the source gas. As illustrated in FIG. 1, the power needle 42 may be disposed in the tube 20. The power needle 42 may be protected from the plasma gas 60 by a first cladding layer 43. As illustrated in FIG. 2, the power ring 44 may surround an outer circumference surface of the tube 20. The tube 20 may be inserted in the power ring 44. The power ring 44 may be a metal ring. The power needle 42 and the power ring 44 may be power electrodes applied with the high frequency power from a power source 10.

The resistor 52 may be connected between the power source 10 and the power needle 42. In other embodiments, the resistor 52 may be connected between the power source 10 and the power ring 44. The resistor 52 may control an impedance value of the high frequency power applied from the power source 10. The resistor 52 may stabilize a current of the high frequency power to prevent the arc discharge of the plasma gas 60. For example, if the impedance value of the resistor 52 is low, a value of the high frequency power may increase. Thus, the plasma gas 60 may be charged in high power. As a result, if the impedance value of the resistor 52 increases, the arc discharge of the plasma gas 60 may be minimized or removed.

The valve 54 may control the source gas supplied into the gas supplying line 22. Additionally, the valve 54 may control the flow rate of the plasma gas 60 outputted from the tube 20. If the flow rate of the source gas flowing in the tube 20 is reduced, the output flow rate of the plasma gas 60 may be reduced. Thus, the charged amount of the plasma gas 60 may increase. Alternatively, if the flow rate of source gas increases, the charged amount of the plasma gas 60 may be reduced. The valve 54 may control the flow rate of the source gas to minimize or remove the arc discharge of the plasma gas 60. The plasma control unit 50 may control the impedance value, and the flow rate of the source gas to remove the arc discharge of the plasma gas 60.

Thus, the plasma jet assembly 100 according to some embodiments of the inventive concept may increase or maximize the stability of the plasma gas 60.

Figure 3:
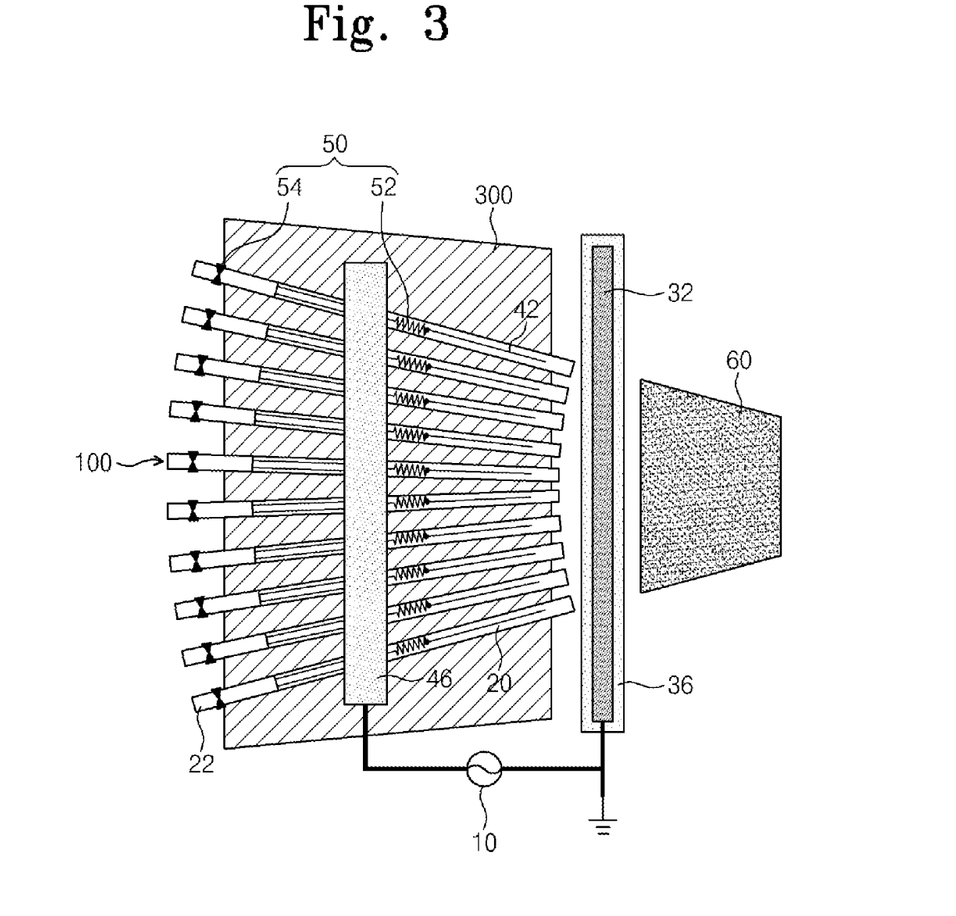
FIG. 3 is a plan view illustrating a plasma brush including plasma jet assemblies of FIG. 1 combined with each other.

FIG. 3 is a plan view illustrating a plasma brush including plasma jet assemblies of FIG. 1 combined with each other.

Referring to FIG. 3, a brush according to embodiments of the inventive concept may include a frame 300 fixing a plurality of plasma jet assemblies 100 and a common ground bar 32. The frame 300 may fix about ten plasma jet assemblies 100 in fan-shape in a horizontal direction. The frame 300 may have a rectangular cross section. The common ground bar 32 may be disposed at an end of the tube 20 which is closer to the plasma gas 60. The common ground bar 32 may be protected from the plasma gas 60 by a second cladding layer 36.

The plasma control units 50 may control the impedance value of the high frequency power and/or the flow rate of the source gas to minimize or remove local arc discharge of the plasma gas 60. As described above, the plasma control units 50 may include the resistors 52 and the valves 54. Each of the resistors 52 may include a variable resistor controlled into impedance values different from each other. The resistors 52 may be ballast resistors. Additionally, the resistors 42 may be connected to a common power electrode 46. The common power electrode 46 may connect the resistors 42 to the power source 10. Here, the resistors 52 may be disposed outside the tubes 20 and power needles 42 may be disposed in the tubes 20. In other embodiments, if the plasma jet assemblies 100 include power rings 44 of FIG. 2, the power rings 44 may be disposed on the outer circumference surfaces of the tubes 20.

Each of the valves 54 may control the flow rate of the source gas or the plasma gas 60 in each of the tubes 20. The valves 54 may be individually controlled for uniformly providing plasma gas 60 in the tubes 20. The valves 54 may determine the output amounts and output angles of the plasma gases 60 respectively outputted from the tubes 20. A planar area of the plasma gas 60 may increase in proportion to the number of the plasma jet assemblies 100. The plasma control units 50 may uniformly and stably provide the large area plasma gas 60 in directions of the plurality of tubes 20.

Thus, the plasma brush according to embodiments of the inventive concept may increase or maximize uniformity of the large are plasma gas 60.

Figure 4:
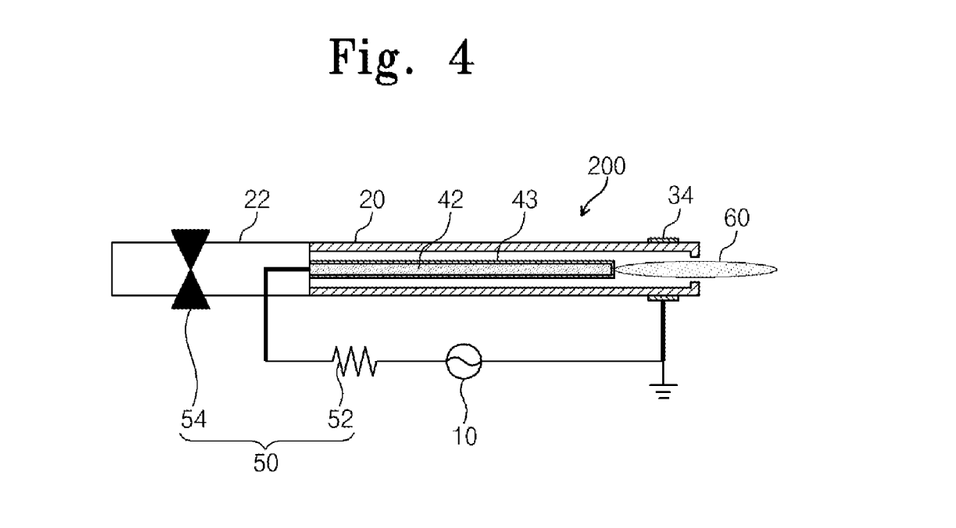
FIGS. 4 and 5 are cross-sectional views illustrating plasma jet assemblies according to other embodiments of the inventive concept.
Figure 5:
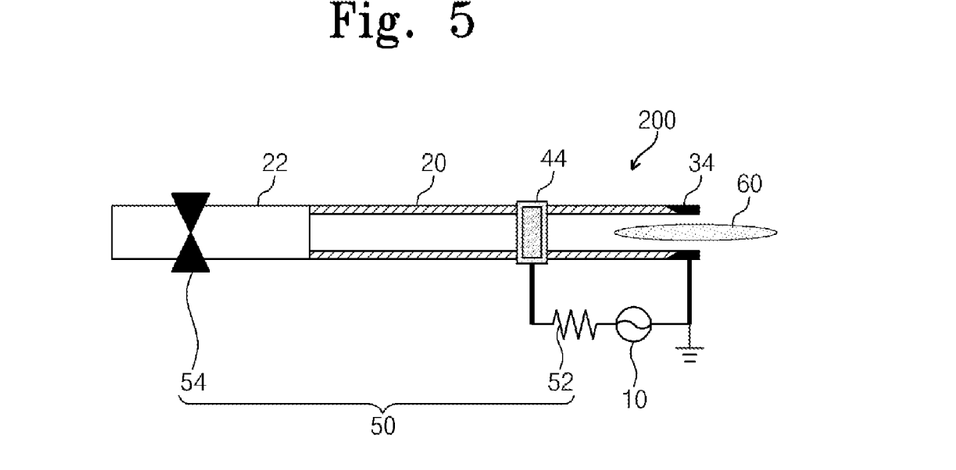

FIGS. 4 and 5 are cross-sectional views illustrating plasma jet assemblies according to other embodiments of the inventive concept.

Referring to FIGS. 4 and 5, a plasma jet assembly 200 according to other embodiments of the inventive concept may include a ground ring 34 disposed at a side of the tube 20 opposite to the power needle 42 or the power ring 44. The ground ring 34 may surround an outer circumference surface. The ground ring 34 may be a metal ring. Alternatively, the ground ring 34 may be combined with an end of the tube 20 or extend from the end of the tube 20. The plasma gas 60 may be generated by a high frequency power induced between the ground ring 34 and the power needle 42. The power source 10 may be connected between the resistor 52 and a ground terminal The power source 10 may provide the high frequency power to the resistor 52, the power needle 42, and the power ring 44.

Thus, the plasma jet assembly 200 according to other embodiments of the inventive concept may minimize or prevent the arc discharge of the plasma gas 60. Even though not shown in the drawings, the plasma jet assemblies 200 according to other embodiments of the inventive concept may constitute a plasma brush generating a large area plasma gas.

Figure 6:
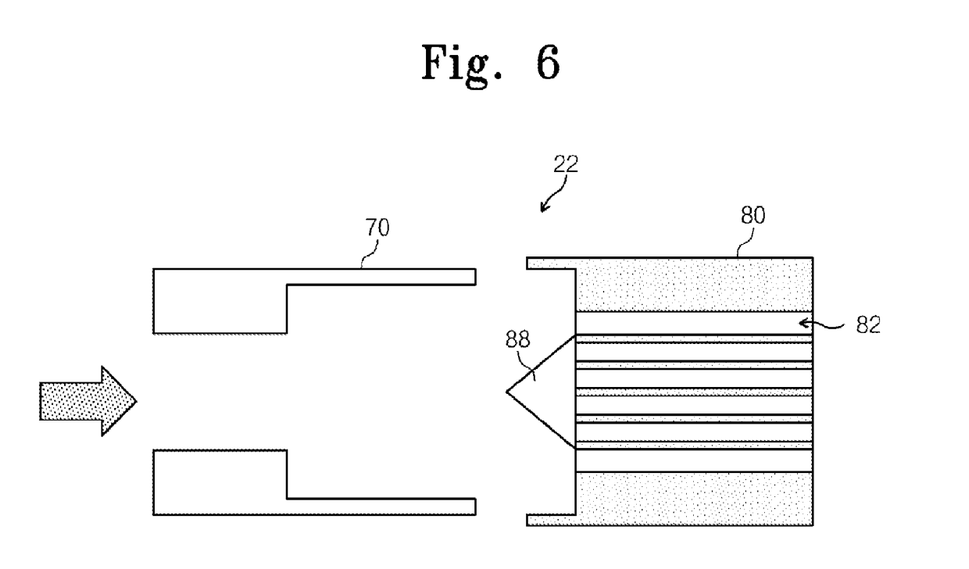
FIG. 6 is a side cross-sectional view illustrating a gas supplying line according to application examples of the inventive concept.
Figure 7:
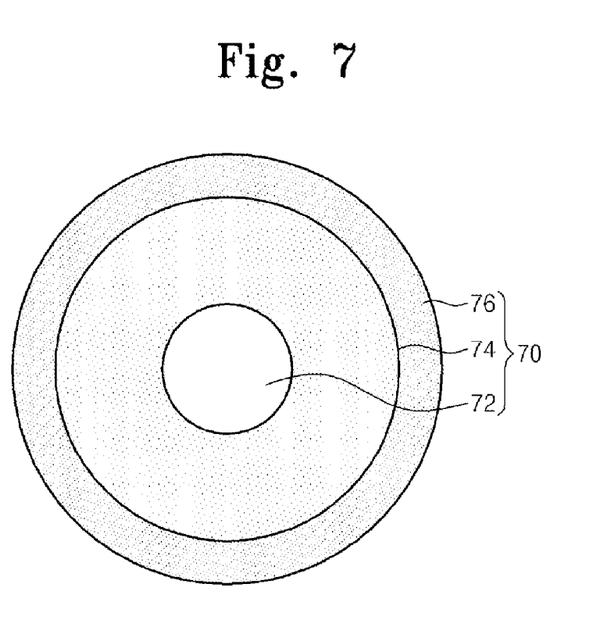
FIG. 7 is a cross-sectional view of a gas line of FIG. 6.
Figure 8:
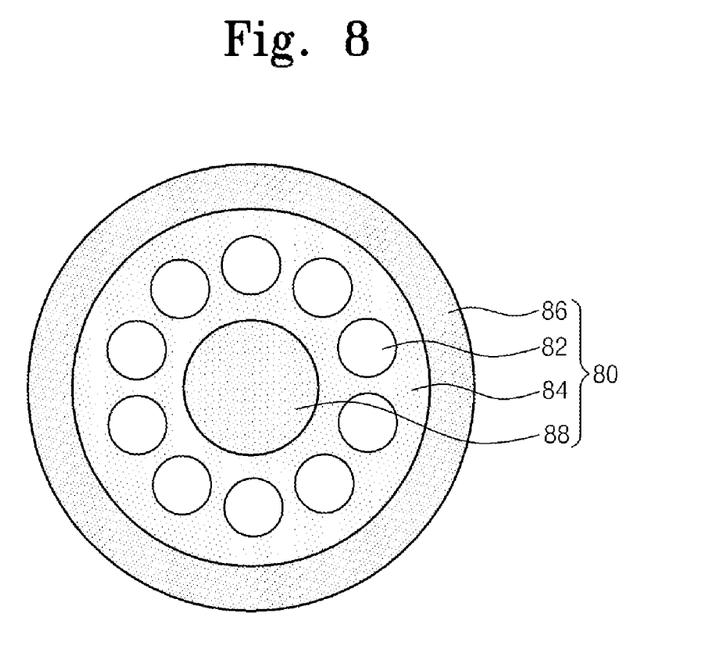
FIG. 8 is a cross-sectional view of a connector of FIG. 6.

FIG. 6 is a side cross-sectional view illustrating a gas supplying line according to application examples of the inventive concept. FIG. 7 is a cross-sectional view of a gas line of FIG. 6. FIG. 8 is a cross-sectional view of a connector of FIG. 6.

Referring to FIGS. 1, 6, 7, and 8, the gas supplying line 22 may include a gas line 70 and a connector 80. The gas line 70 may include a first pipe 74 having a hollow hole 72 through which a gas flows, and a third cladding layer 76 surrounding the first pipe 74. The hollow hole 72 of an end portion of the first pipe 74 may be enlarged in a trumpet-shape. The gas line 70 may be connected to the connector 80.

The connector 80 may be combined with the tube 20. The connector 80 may include a second pipe 84 having channel holes 82 formed around an insulating stick 88. The channel holes 82 may be disposed around the insulating stick 88 in the second pipe 84. The channel holes 82 may be symmetrically formed with respect to the insulating stick 88. For example, about ten channel holes 82 may be disposed around the insulating stick 88. The first pipe 74 may be inserted in the second pipe 84. The insulating stick 88 of the second pipe 84 may be inserted in the hollow hole 72. A fourth cladding layer 86 may be disposed on an outer circumference surface of the second pipe 84.

The first pipe 74 and the second pipe 84 may include a dielectric material, plastic, rubber, or polymer. The gas line 70 and the connection 80 may supply the source gas of uniform pressure into the tube 20. Even though not shown in the drawings, valves individually controlling gas supply may be installed at the channel holes 82, respectively.

Thus, the gas supplying line 22 according to application examples of the inventive concept may provide the gas of uniform pressure into the tube 20.

According to embodiments of the inventive concept, the plasma jet assembly may include the plasma control unit removing or minimizing the arc discharge of the plasma gas. The plasma control unit may include the resistor connected between the power electrode and the power source. Additionally, the plasma control unit may include a gas control valve controlling the flow rate of the plasma gas.

Thus, the plasma jet assembly and the plasma brush may increase or maximize the stability of the large area plasma gas.

While the inventive concept has been described with reference to example embodiments, it will be apparent to those skilled in the art that various changes and modifications may be made without departing from the spirit and scope of the inventive concept. Therefore, it should be understood that the above embodiments are not limiting, but illustrative. Thus, the scope of the inventive concept is to be determined by the broadest permissible interpretation of the following claims and their equivalents, and shall not be restricted or limited by the foregoing description.

What is claimed is:

1. A plasma jet assembly comprising:
   a tube having a proximate end and a distal end through which a gas flows;
   a power source providing a high frequency power exciting the gas into a plasma state;
   a power needle electrode applying the high frequency power to the gas in the tube, wherein the power needle electrode is disposed inside the tube and connected to the power source;
   a ground ring disposed around the distal end of the tube, said ground ring connected to the power source;
   a plasma control unit including
      a resistor disposed between the power source and the power needle electrode,
      a connector having a first end and a second end, a gas supplying line connected to the proximate end of the tube with the connector, and
a gas control valve controlling a flow rate of the gas flowing into the tube, said gas control valve disposed in the gas supplying line,
wherein an end of the gas supplying line is inserted into the first end of the connector,
wherein the second end of the connector is connected to the proximate end of the tube,
wherein the gas flows from the gas supplying line through the connector and into the tube, and
wherein the connector includes
a cylindrical pipe extending axially from the first end to the second end of the connector,
wherein the pipe includes a plurality of gas channels formed and arranged radially in the pipe wall, the gas channels extending axially from the first end to the second end of the connector to deliver gas into the tube, and
an insulating stick disposed axially within the pipe,
wherein arc discharge of a plasma gas generated in the tube by the high frequency power applied to the power needle electrode is controlled by adjustment of an impedance value of the high frequency power by the resistor and by control of the flow rate of the gas by the gas control valve.

2. The plasma jet assembly of claim 1, wherein the power needle electrode further includes a cladding layer protecting the needle from the plasma gas.

3. The plasma jet assembly of claim 1, wherein the tube includes a dielectric material.

4. The plasma jet assembly of claim 3, wherein the dielectric material includes alumina or ceramic.

5. The plasma jet assembly of claim 1, wherein the gas supplying line includes a second pipe having a hollow hole through which gas flows, and hollow hole at the end of the gas supplying line inserted into the first end of the connector is enlarged in a trumpet-shape.

6. The plasma jet assembly of claim 5, wherein a cladding layer surrounds the second pipe.

7. A plasma brush comprising:
a frame;
a power source providing a high frequency power exciting gas into a plasma state; and
a plurality of plasma jet assemblies fixed in the frame, wherein each of the plasma jet assemblies includes
a tube having a proximate end and a distal end through which a gas flows,
a power electrode applying the high frequency power to the gas in the tube, wherein the power electrode is coupled with the tube and connected to the power source,
a plasma control unit including
a resistor disposed between the power source and the power electrode,
a connector having a first end and a second end,
a gas supplying line connected to the proximate end of the tube with the connector, and
a gas control valve controlling a flow rate of the gas flowing into the tube, said gas control valve disposed in the gas supplying line,
wherein an end of the gas supplying line is inserted into the first end of the connector,
wherein the second end of the connector is connected to the proximate end of the tube,
wherein the gas flows from the gas supplying line through the connector and into the tube, and
wherein the connector includes
a cylindrical pipe extending axially from the first end to the second end of the connector,
wherein the pipe includes a plurality of gas channels formed and arranged radially in the pipe wall, the gas channels extending axially from the first end to the second end of the connector to deliver gas into the tube, and
an insulating stick disposed axially within the pipe,
wherein arc discharge of a plasma gas generated in the tube by the high frequency power applied to the power electrode is controlled by adjustment of an impedance value of the high frequency power by the resistor and by control of the flow rate of the gas by the gas control valve, and
a common ground bar located outside of the frame at the distal end of the tube of each of the plurality of plasma jet assemblies.

8. The plasma brush of claim 7, further comprising:
a cladding layer protecting the common ground bar from the plasma gas.

9. The plasma brush of claim 7, further comprising a common power electrode for the plurality of plasma jet assemblies connected between the power source and the resistors, and wherein the power electrode is a needle electrode disposed inside the tube.

10. The plasma brush of claim 7, wherein the power electrode is a ring electrode disposed around the tube.

11. The plasma brush of claim 7, wherein each resistor is a ballast resistor.

12. The plasma brush of claim 7, wherein ten plasma jet assemblies are fixed in the frame.

13. The plasma brush of claim 7, wherein the frame has a rectangular cross section.

14. The plasma brush of claim 7, wherein the plurality of plasma jet assemblies are fixed in the frame in a horizontal direction and in a fan-shape.

15. A plasma jet assembly comprising:
a tube having a proximate end and a distal end through which a gas flows;
a power source providing a high frequency power exciting the gas into a plasma state;
a power electrode applying the high frequency power to the gas in the tube, wherein the power electrode includes a metal ring disposed around the tube and connected to the power source;
a ground electrode disposed near the distal end of the tube, said ground electrode connected to the power source;
a plasma control unit including
a resistor disposed between the power source and the power electrode,
a connector having a first end and a second end,
a gas supplying line connected to the proximate end of the tube with the connector,
a gas control valve controlling a flow rate of the gas flowing into the tube, said gas control valve disposed in the gas supplying line,
wherein an end of the gas supplying line is inserted into the first end of the connector,
wherein the second end of the connector is connected to the proximate end of the tube, and
wherein the gas flows from the gas supplying line through the connector and into the tube, and
wherein the connector includes
a cylindrical pipe extending axially from the first end to the second end of the connector, wherein the pipe includes a plurality of gas channels formed and arranged radially in the pipe wall, the gas channels extending axially from the first end to the second end of the connector to deliver gas into the tube, and an insulating stick disposed axially within the pipe, wherein arc discharge of a plasma gas generated in the tube by the high frequency power applied to the power electrode is controlled by adjustment of an impedance value of the high frequency power by the resistor and by control of the flow rate of the gas by the gas control valve.

16. The plasma jet assembly of claim 15, wherein the ground electrode is a ground ring disposed around the tube.

17. The plasma jet assembly of claim 15, wherein the ground electrode is a ground ring formed at the distal end of the tube.

18. The plasma jet assembly of claim 15, wherein the power electrode further includes a cladding layer protecting the power electrode from the plasma gas.

19. The plasma jet assembly of claim 15, wherein the tube includes a dielectric material.

20. The plasma jet assembly of claim 19, wherein the dielectric material includes alumina or ceramic.

* * * * *